(12) United States Patent
Smith et al.

(10) Patent No.: US 9,649,089 B2
(45) Date of Patent: May 16, 2017

(54) PORTABLE ULTRASOUND SCANNER AND DOCKING SYSTEM

(75) Inventors: Johannes Anders Smith, Hellerup (DK); Ole Christian Jensen, Værløse (DK)

(73) Assignee: B-K Medical Aps, Herlev (DK)

( * ) Notice: Subject to any disclaimer, the term of this patent is extended or adjusted under 35 U.S.C. 154(b) by 998 days.

(21) Appl. No.: 12/619,797

(22) Filed: Nov. 17, 2009

(65) Prior Publication Data

US 2011/0118562 A1    May 19, 2011

(51) Int. Cl.
*A61B 8/00* (2006.01)
*A61B 5/00* (2006.01)

(52) U.S. Cl.
CPC .............. *A61B 8/00* (2013.01); *A61B 8/4411* (2013.01); *A61B 2560/0456* (2013.01)

(58) Field of Classification Search
USPC ........ 340/539.12; 361/679.41; 600/437, 440, 600/441, 443, 446, 459, 509
See application file for complete search history.

(56) References Cited

U.S. PATENT DOCUMENTS

| | | | |
|---|---|---|---|
| 6,256,193 B1 * | 7/2001 | Janik ..................... | A47B 23/043 248/922 |
| 6,352,511 B1 * | 3/2002 | Hossack et al. ............... | 600/443 |
| 6,364,839 B1 * | 4/2002 | Little et al. ................... | 600/459 |
| 6,447,451 B1 * | 9/2002 | Wing et al. .................... | 600/437 |
| 6,569,101 B2 * | 5/2003 | Quistgaard et al. .......... | 600/459 |
| 6,575,908 B2 * | 6/2003 | Barnes et al. ................. | 600/443 |
| 6,962,566 B2 * | 11/2005 | Quistgaard et al. .......... | 600/437 |
| 7,115,093 B2 * | 10/2006 | Halmann et al. ............. | 600/437 |
| 7,301,451 B2 * | 11/2007 | Hastings .................. | 340/539.12 |
| 7,352,570 B2 * | 4/2008 | Smith et al. ............. | 361/679.41 |
| 7,549,961 B1 * | 6/2009 | Hwang ......................... | 600/440 |
| 7,819,807 B2 * | 10/2010 | Barnes et al. ................. | 600/443 |
| 8,043,217 B1 * | 10/2011 | Rambod ........................ | 600/438 |
| 2002/0143256 A1 * | 10/2002 | Wing et al. .................... | 600/459 |
| 2003/0078501 A1 * | 4/2003 | Barnes et al. ................. | 600/446 |
| 2003/0195418 A1 * | 10/2003 | Barnes et al. ................. | 600/437 |
| 2004/0138569 A1 * | 7/2004 | Grunwald et al. ............ | 600/459 |
| 2004/0152982 A1 * | 8/2004 | Hwang ............... | G01S 7/52079 600/441 |
| 2004/0159757 A1 * | 8/2004 | Pfister ........................ | 248/284.1 |
| 2004/0186357 A1 * | 9/2004 | Soderberg ................ | A61B 5/00 600/300 |
| 2005/0124890 A1 * | 6/2005 | Halmann et al. ............. | 600/446 |
| 2005/0146431 A1 * | 7/2005 | Hastings et al. ......... | 340/539.12 |
| 2005/0148890 A1 * | 7/2005 | Hastings ....................... | 600/509 |
| 2005/0251035 A1 * | 11/2005 | Wong et al. ................... | 600/437 |
| 2006/0025684 A1 * | 2/2006 | Quistgaard et al. .......... | 600/441 |
| 2007/0239001 A1 * | 10/2007 | Mehi et al. .................... | 600/437 |
| 2008/0146922 A1 * | 6/2008 | Steins et al. .................. | 600/437 |
| 2009/0131793 A1 * | 5/2009 | Stonefield et al. ........... | 600/443 |
| 2010/0016726 A1 * | 1/2010 | Meier ........................... | 600/459 |

* cited by examiner

*Primary Examiner* — Serkan Akar
(74) *Attorney, Agent, or Firm* — Anthony M. Del Zoppo, III; Driggs, Hogg, Daugherty & Del Zoppo, Co. LPA

(57) ABSTRACT

An apparatus includes a plurality of portable scanners and docks. The scanners include first and second configurations to provide different functionality. The docks include at least one of floor, a wall, and a table dock. The scanners are selectively mateable to the various docks.

11 Claims, 4 Drawing Sheets

PORTABLE ULTRASOUND SCANNER AND DOCKING SYSTEM

BACKGROUND

Figure 1:
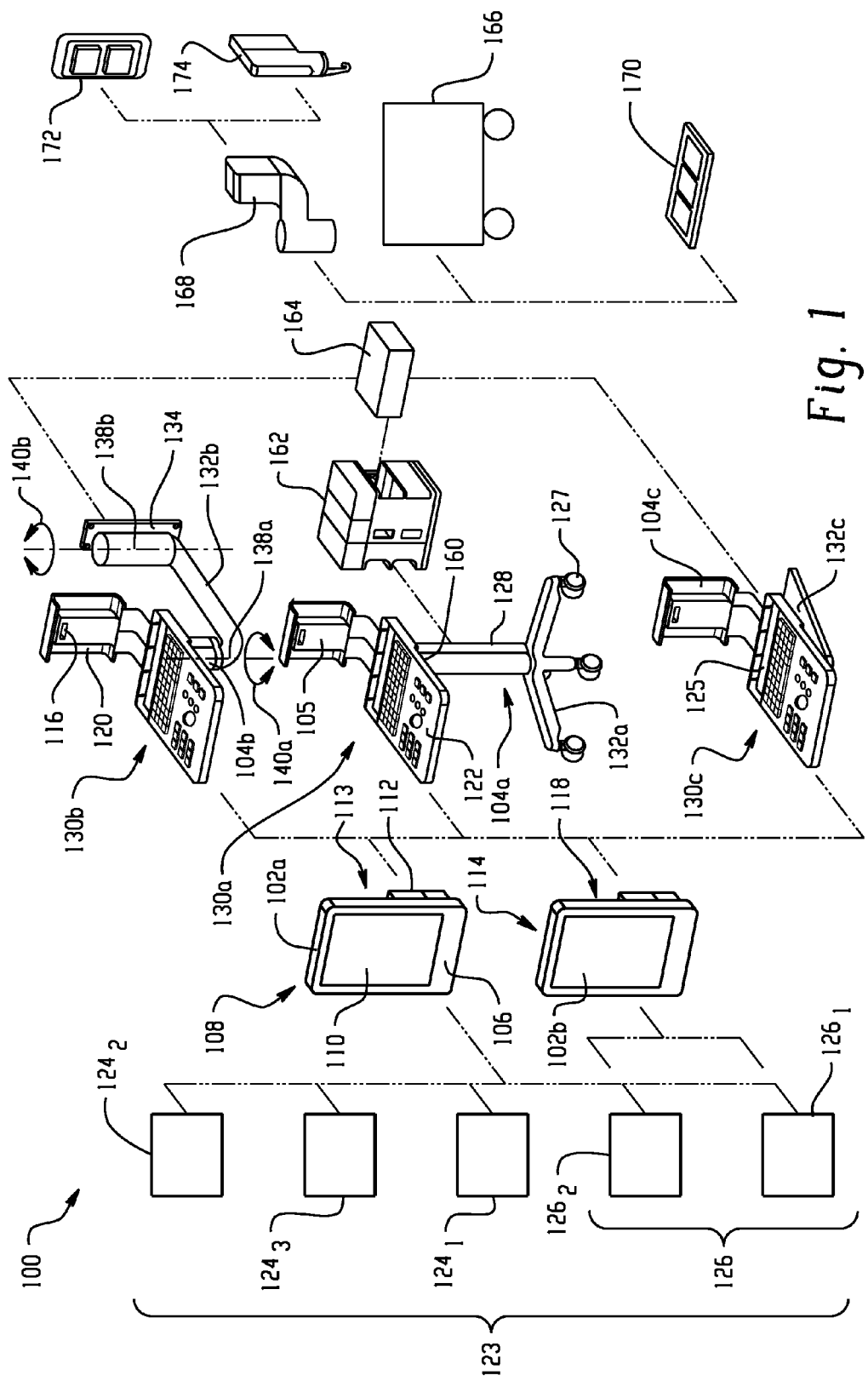

The present application relates to physiological monitoring devices. While it finds particular application to ultrasound scanners in medical and veterinary applications, it also applies to the monitoring of other physiological variables.

Ultrasound scanners provide useful information about the interior characteristics of an object under examination. In medical applications, clinicians have used ultrasound scanners to examine human subjects in settings such as hospitals, physician's offices, and other locations. Ultrasound scanners have been used in the emergency room, operating room, and similar environments.

Other types of physiological variable scanners are also known. Examples include blood pressure, respiration, cardiac, glucose, and oxygen saturation monitors.

Applications for these scanners often place a premium on size and convenience. In an operating room, for example, space is often at a premium, and the scanner may come into contact with bodily fluids. Moreover, it is sometimes desirable to transport the scanner from room-to-room. To this end, portable scanners have been equipped with wheeled carts that allow the scanner to be rolled along the floor.

Other scanners have taken the generally clam-shell form factor of a laptop computer, with a display hingedly attached to a keyboard. The necessary interfaces have been included in the laptop-like unit so that the transducers, input output devices, and other peripherals can be connected to the laptop like unit as needed. These scanners are configured to be placed on a relatively flat surface such as a tabletop, the surface of a wheeled utility cart, or the like. Unfortunately, such a surface is not always readily available or may be inconvenient. The external interface connections also tend to be relatively inconvenient.

SUMMARY

Aspects of the present application address the above matters, and others.

According to a first aspect of the present application, a system includes a first dock including a first portion and a base portion. The first portion of the first dock includes a user interface and a power supply. The base portion of the first dock is configured to support the first portion of the first dock relative to a first surface. The system also includes a second dock including a first portion and a base portion. The first portion of the second dock includes a user interface and a power supply. The base portion of the second dock is configured to support the second portion of the second dock relative to a second surface. The systems also includes first portable ultrasound scanner including an ultrasound transducer interface, a display, and a dock interface that selectively connects the first scanner to the first and second docks for operation in conjunction therewith.

According to another aspect of the present application, an apparatus includes a first portable scanner including an ultrasound transducer interface, a display, and a dock interface that selectively connects the first scanner to a dock for operation in conjunction therewith. The apparatus also includes a second portable scanner including a transducer interface, a display, and a dock interface that selectively connects the first scanner to the first and second docks for operation in conjunction therewith. The apparatus also includes a first dock including a scanner interface that selectively receives the first and second scanners. The first dock includes a user interface that varies an operation of a scanner received by the first dock. The second portable scanner is configured to provide functionality different from the functionality of the first portable scanner.

According to another aspect of the present invention, a method includes installing a first portable scanner on a first scanner dock, using the first scanner to perform a first desired function, detaching the first portable scanner from the first dock, installing the first portable scanner on a second dock, and using the first scanner to perform a second different desired function.

Those of ordinary skill in the art will appreciate still other aspects of the present invention upon reading and understanding the appended description.

FIGURES

Figure 2:
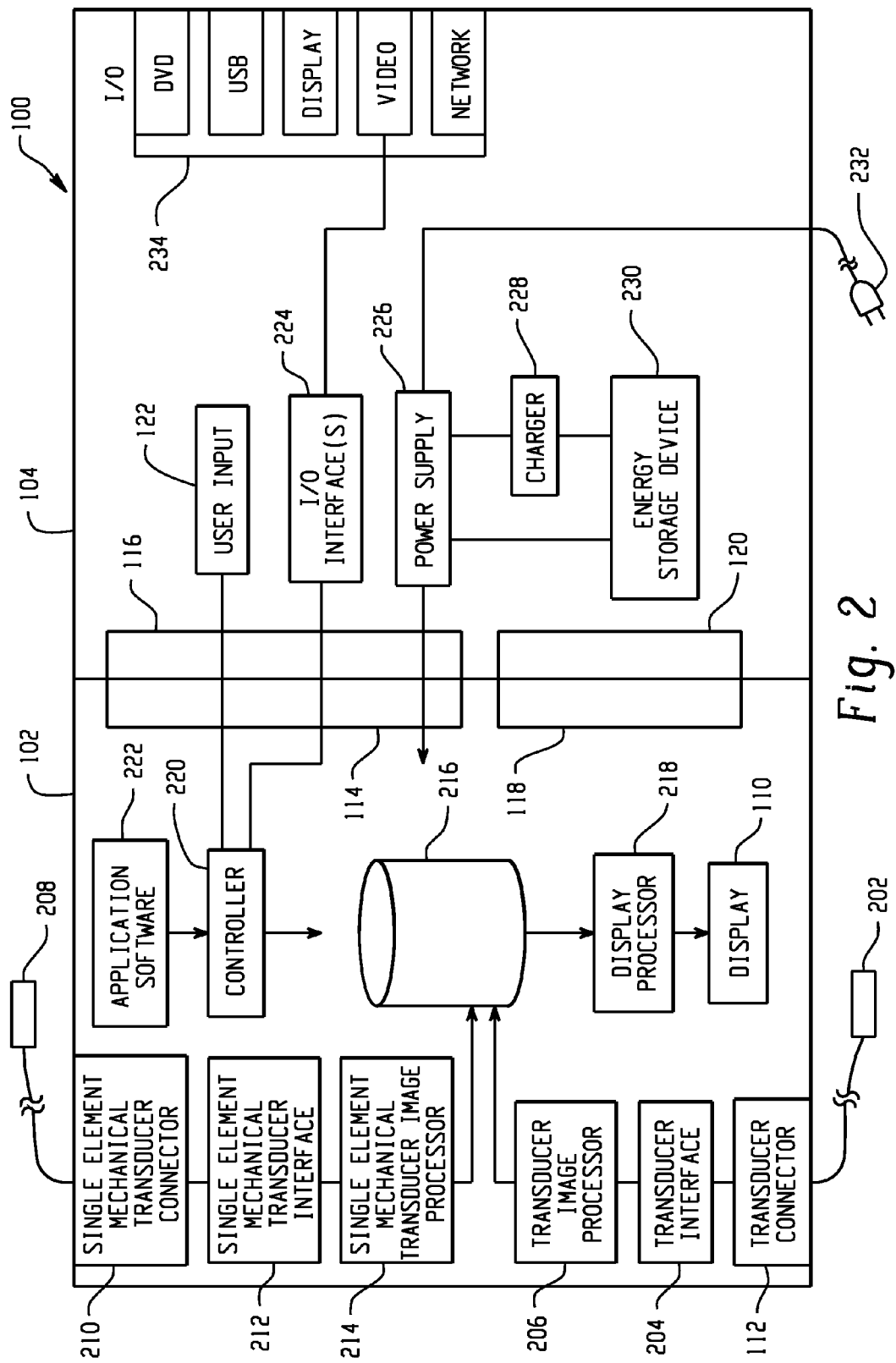
Figure 3:
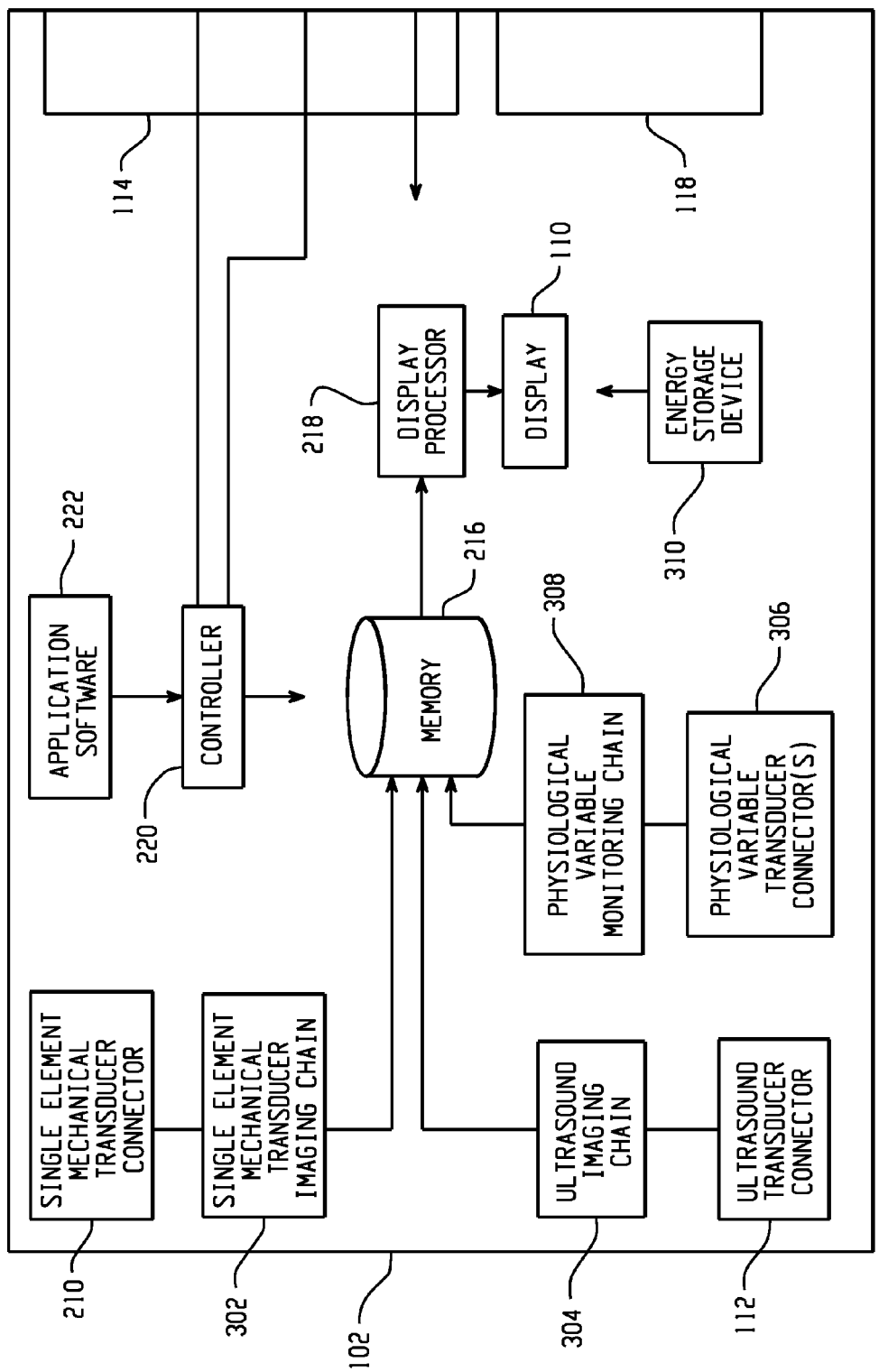
Figure 4:
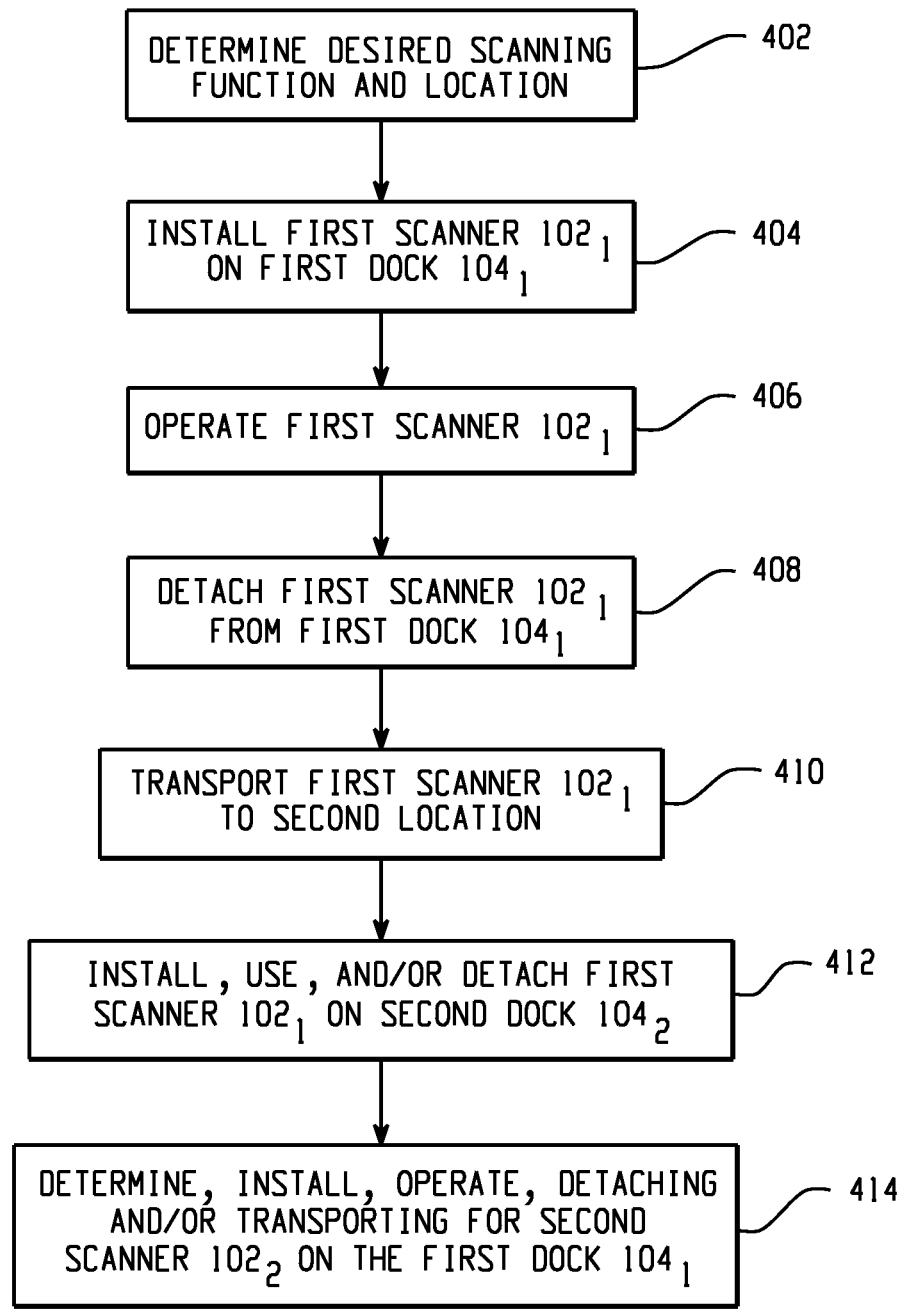

The application is illustrated by way of example and not limitation in the figures of the accompanying drawings, in which like references indicate similar elements and in which:

FIG. 1 depicts an ultrasound scanner.
FIG. 2 is a functional block diagram of an ultrasound scanner.
FIG. 3 is a functional block diagram of a scanner.
FIG. 4 depicts a scanning method.

DESCRIPTION

With reference to FIG. 1, an ultrasound imaging apparatus 100 includes one or more portable ultrasound scanners 102a, 102b that selectively mate with one or more docks such as a floor dock 104a, a wall dock 104b, and a table dock 104c.

In the illustrated implementation, the form factors of the scanners 102a, 102b are substantially identical. Each scanner 102 includes front 106 and rear 108 major surfaces. A human readable display 110 such as a flat panel LCD display is visible from the front surface 106. Also as illustrated, the displays 110 and scanners 102 are oriented in the portrait mode, with each having a vertical dimension greater than its respective horizontal dimension.

An ultrasound transducer connector 112 located at a side of each scanner 102 is configured to connect to the corresponding connector of an ultrasound transducer. The scanners 102 may also include a single element mechanical transducer connector for connecting to a single element mechanical transducer. In one implementation, the displays 110 have respective diagonal, vertical and horizontal dimension of about 19 inches (48.3 cm).

The scanners 102 include a dock interface 113 for connecting the scanners 102 to the various docks 104. One or more electrical connectors 114 located at the rear 108 of the scanners 102 are configured to connect to corresponding connector(s) 116 of the docks 104. One or more mechanical connectors 118 also located to the rear 108 of the scanners 102 allow the user to selectively attach the scanners 102 to a connector 120 of a desired dock 104. The mechanical connectors 118 may take the form of a user operable latch, a dock 104 mounted sleeve that accepts the scanners 102, or the like. It will be appreciated that the electrical 114 and mechanical 118 connectors may be configured in a single connector. In the illustrated implementation, the scanners 102 are functional only when mated to a dock 104.

As illustrated in FIG. 1, the scanners 102 are configured to provide different functionality 123. For examples, in one embodiment one of the scanners 102 is a full-featured scanner supporting a set of applications including single element mechanical transducer functionality, another of the scanners 102 is a lower functionality scanner supporting a subset of the set of applications (e.g., without single element mechanical transducer functionality), another of the scanners 102 is a dedicated scanner such as a scanner that supports surgical transducers for surgical applications, and another of the scanners 102 is a lower functionality dedicated scanner supporting a subset of the surgical applications. Other scanners with other functionality are also contemplated herein. The particular applications supported by a scanner 102 may be predetermined and/or purchasable software applications and/or hardware.

By way of another example, the first scanner 102a may perform a first set 124 of functions, and the second scanner 102b may perform a second set 126 of functions, where the second set 126 is a subset of the first set 124. The second set 126 may include a relatively basic set of functions such as digital information and communication in medicine (DICOM) $126_1$ communication and color flow mode (CFM) $126_2$ imaging capabilities. The first set 124 may include the functions of the second set 126, as well as other desired functions such as three dimensional image rendering and/or manipulation $124_1$, a brachytherapy interface $124_2$, an endoscopy interface $124_3$, or similar capabilities. In another instance, the second set of functions 126 is different from the first set of functions 124.

Different versions of the scanners 102 may each be configured to perform ultrasound imaging functions used in one or more different medical specialties such as urology, anesthesiology, general radiology, or the like. Thus, for example, different scanners 102 may be configured to include functionality typically required in one or more of urological ultrasound, anesthesiology, gastroenterology, surgery, general radiology, and so on. For example, a urological scanner may be configured to interface with a transrectal or transvaginal probe and/or provide user interface functionality typically required in urological applications; a gastroenterological scanner may be configured to interface with a transesophogeal probe and provide user interface functionality typically required in gastroenterological applications, an anesthesiology scanner may be configured to guide the application of an epidural or nerve block under substantially real time ultrasound image guidance, and so on.

With continuing reference to FIG. 1, the docks 104 include a common portion 130 and a base portion 132. As illustrated, the common portions 130a, 130b, 130c of the respective docks 104a, 104b, 104c have the same form factor and are substantially mechanically and electrically identical. The base portions 132a, 132b, 132c are configured to support the common portions 130a, 130b, 130c relative to a desired surface.

The common portions 130 include a user input device or interface 122, a scanner interface 105 and one or more transducer holders 125 that are configured to hold ultrasound transducers that are not in use. In one embodiment, the one or more transducer holders 125 are omitted from at least one of the common portions 130. The user interface 122 includes an input device such as a keyboard, a trackball, a trackpad, a touch-based interface, and/or other input device. The docks 104 receive the scanners 102 generally in the region of the scanner interface 105, which includes mechanical and/or electrical interfaces corresponding to those on the scanners 102. The common portions 130 also include various input/output (I/O) devices such as a DVD drive or slot, universal serial bus (USB) port, wired or wireless network interfaces for communicating with a picture archiving and communications system (PACS), hospital information system/radiology information system (HIS/RIS), auxiliary display or video interfaces, or the like.

The common portions 130 also include a power supply that provides power to a scanner 102. The power supply may be located in the region of the scanner interface 105 (e.g., generally behind the scanner 102), in the arm that supports the scanner 102, or in the region of the user interface 122.

The base portion 132a of floor dock 104a supports the common portion 130a of the dock 104a relative to a floor or other similar surface. As illustrated, the floor dock 104a includes four (4) or another desired number of wheels 127 located on supports extending radially from a vertical post 128 that supports the common portion 130a relative to the floor. In one implementation, the post 128 is telescoping or otherwise adjustable to at least a high and a low position. At the low position, the top of a scanner 102 mated to the floor dock 104a is at a height that allows an average user to see over the top of the scanner 102 when rolling the unit across the floor.

In one implementation, the low position is selected so that the top of the scanner 102 is about 53 inches (135.0 cm) from the floor. At the high position, the display 110 of a scanner 102 mated to the floor dock 104a is located at approximately eye level of a standing human user. In one implementation, the high position is selected so that the midpoint of the display 110 is about 63 inches (160.2 cm) from the floor. Still other relatively higher, lower, and intermediate positions are contemplated. As one example, the height may be adjustable so that the keyboard 122 and display 110 are convenient for a user seated in a typical chair.

An accessory mount 160 is located generally to the rear of the post 128, for example by way of a flat surface. An accessory holder 162 removably attaches to the accessory mount 160. The accessory holder 162 likewise removably carries one more accessory devices such as a printer 164. Suitable electrical connections provide power and signal connections so that the accessory devices operate in conjunction with a scanner attached to the dock 104a. Preferably, at least one of the accessory holders 162 and the printer 164 are readily attachable and detachable from the dock 104a without tools.

The base 132c of the table dock 104c supports the common portion 130c relative to a table, desktop, or other similar surface. As illustrated, the base 132c rests on or otherwise supports the dock 104c on the surface.

The base 132b of the wall dock 104b supports the scanner 102 relative to a vertical surface such as a wall. A wall mount 134 located at the distal end of the wall base 132b is used to fasten the wall dock 104b to the wall. The common portion 130b is located at the proximal end of the wall dock 104b. As illustrated, the wall dock 104b includes first 138a and second 138b pivots located near the proximal and distal ends, respectively. The pivots 138 are configured to pivot about substantially vertical axes of rotation 140a, 140b, thereby allowing the proximal end of the dock 104b to be located relatively nearer to or farther from the wall, while allowing the common portion 130b to face in a desired direction relative to the wall. Vertical or other adjustments are also contemplated.

Ceiling, vehicular, or other docks 104 are also contemplated.

A wheeled transport case 166 receives the accessory holder 162 and/or the accessories 164 and facilitates transport of the accessories. Where used with a wall 104b, table 104c, or other dock, electrical connections may be provided as desired, for example through suitable cabling. Other accessories such as a endoscopic transducer holder 168 or a foot switch 170 may also be included in the system 100 and likewise be transported. Other accessories such as a transducer wall mount 172 and a transducer holder wall mount 174 may also be provided to facilitate transducer handling and cable management, particularly for transducers not in use.

FIG. 2 is a functional block diagram of an ultrasound imaging apparatus 100 including a scanner 102 and a dock 104. The scanner 102 includes ultrasound imaging functionality and single element mechanical transducer support.

Turning first to the ultrasound imaging chain, a transducer interface 204 interfaces with an ultrasound transducer 202 connected to the connector 112. The configuration and functionality of the transducer 202 and transducer interface 204 are typically application dependent.

A transducer image processor 206 in operative communication with the transducer interface 204 generates three-dimensional (3D) or other ultrasound image data indicative of an object under examination for storage in a suitable computer readable memory 216.

Turning to the single element mechanical transducer imaging chain, a single element mechanical transducer interface 212 interfaces to an single element mechanical transducer 208 connected to single element mechanical transducer connector 210. An ultrasound image processor 214 in operative communication with the single element mechanical interface 212 generates image data indicative of an object under examination for storage in the memory 216.

A display processor 218 processes the ultrasound image data for display on the display 110. Processing and display of the ultrasound typically occur in substantially real time during the course of an examination of an object.

A controller 220 such as a microprocessor or microcontroller controls the operation of the scanner 102. Application software 222 is configured to provide the functions 124, 126 or other desired application functionality.

The electrical connector 116 provides electrical connections between the scanner 102 the dock-mounted devices such as the user input 122, the I/O interface(s) 224 and the power supply 226.

The power supply 226 receives power from an external power source such as 120/240 Vac power mains, vehicular power source, or the like through a line cord or other electrical connection 232 and provides electrical power at the voltage and current levels required by the apparatus 100. The dock 104 may also include a rechargeable energy storage device 230 such as a rechargeable battery to provide operating power while the dock 104 is not connected to an external power source. A charger 228 charges the energy storage device 230.

In one implementation, the energy storage device 230 provides sufficient energy to power the scanner for only a relatively short period of time, for example on the order of less than about sixty (60) minutes. In the case of the floor dock 104a, such an implementation allows the unit to be moved from room to room without completely de-powering the scanner 102. The scanner 102 may also enter a reduced power or sleep mode when external power is not available or the dock 104 is otherwise not connected to the external power source. The dock 104 also includes desired I/O interface(s) 224 and connection(s) 234 such as those for one or more of a DVD, USB, display, video, digital communication network, or the like.

FIG. 3 depicts a second implementation of a portable scanner 102. The scanner 102 includes single element mechanical transducer 302 and ultrasound 304 imaging chains generally as described above in connection with FIG. 2. The scanner 102 also includes one or more physiological variable transducer connectors 306 and physiological variable monitoring chains 308. The physiological variable(s), which are typically presented on the display 110 in substantially real time, may include variables such as pulse rate, blood pressure, oxygen saturation, glucose, cardiac characteristics such as cardiac function or output, or electrocardiogram (EKG) signals, respiration or the like. The scanner 102 also includes an energy storage device 310 so that the scanner may be operated independently of a dock 104. The device may be also configured so that the scanner 102 is substantially non-operational but remains in a suspend mode when not so connected.

Variations are contemplated. The various signal chains may be implemented in any combination. For example, versions of the scanner 102 may include both ultrasound imaging and single element mechanical transducer support, single element mechanical transducer support standing alone, ultrasound capability standing alone, or the like. Different versions of the scanner 102 may be configured to measure physiological variable(s) in differing combinations. In another variation, the scanner 102 may include user-replaceable modules such as cards or pods that allow the user to configure the scanner 102 to provide desired functionally (e.g., modules specific to a particular variable or transducer type Versions of the scanner 102 may also have differing exterior form factors. Preferably, however, the various scanners 102 are configured to be electrically and mechanically interchangeable among the various docks 104. Versions of the scanner 102 may also include user input functionality similar to user input 122, implemented for example by way of a touch screen implemented on the display 110. In a related variation, the user input 122 may be omitted from one or more versions of the dock 104. The controller 220 senses or otherwise determines if the scanner 102 is connected to a dock 104 that does not include a user input 122, in which case the scanner 102 operates via its internal user input.

In another implementation, the ultrasound transducer 202 includes a bi-plane or tri-plane transducer. A bi-plane transducer acquires image information in two planes or directions; a tri-plane transducer acquires imaging information in three planes or directions. In the case of a bi-plane transducer, the two images can be presented simultaneously on the display 110. Where the display 110 is configured in the portrait mode, the two images can be displayed in a vertically stacked arrangement, with one of the images being located physically above the other. Where the display 100 is sized substantially as described above, the size of the presented images can be relatively large.

Similar results can be achieved with a tri-plane transducer, although the simultaneous presentation of three images may require that the images be somewhat smaller or the display 110 relatively larger. Similar results may also be achieved in the case of single plane transducers. It will also be appreciated that similar displays may be implemented where the scanner 102 is configured to simultaneously present a combination of two or more of ultrasound, physiological, or endoscopic data. It will also be appreciated that, for a given display 110 size, the portrait arrangement tends to reduce the footprint of the scanner 102.

The scanner 102 and dock 104 configuration may be exploited in various ways. For example, depending on factors such as the time of day, the patient(s) being seen, or the type of scan to be performed at a given location, the physician or other user may select a scanner 102 having the desired functionality and install it on the available dock 104. Similarly, the user may employ a particular scanner 102 at each of a number of locations. As another example, the user may readily transport a single scanner 102 for use in a plurality of locations or readily upgrade the scanner 102 as his or her needs change. In locations where space is particularly valuable, the user may install a dock 104 that does not include a user input.

An operation of the apparatus 100 will now be described in relation to FIG. 4. At 402, the user determines a desired scanning function to be conducted at a first location. For the purposes of the present example, it will be assumed that the user desires to conduct an ultrasound imaging scan. It will also be assumed that the first location is an examination room that contains a first wall dock 104$_1$.

At 404, the user installs a first scanner 102$_1$ that performs the desired scanning functions on the first dock 104$_1$. If not already connected, the user connects the requisite transducers to the first scanner 102$_1$.

At 406, the user operates the first scanner 102$_1$ as desired. For example, the user may conduct transrectal ultrasound examination of one or more human patient(s).

At 408, the user detaches the first scanner 102$_1$ from the first dock 104$_1$. If not already detached, the user may elect to detach the requisite transducers from the first scanner 102$_1$.

At 410, the user transports the first scanner 102$_1$ to a second location that includes a second dock 104$_2$. For the purposes of the present example, it will be assumed that the second dock 104$_2$ includes a floor dock 104$c$.

At 412, the user performs the steps of installing, using, and/or detaching the first scanner 102$_1$ from the second dock 104$_2$ in a manner similar to steps 404, 406, 408 above. It will be appreciated that the particular examination and the object on which it is performed may be different.

At 414, the same or a different user may perform the steps of determining, installing, operating, detaching, and or transporting for a second scanner 102$_2$ on the first dock 104$_1$.

Those of ordinary skill in the art understand that numerous other permutations of the above are possible.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A system comprising:
   a first dock including a first common portion and a base portion, wherein the first common portion of the first dock includes a support member with a first end region, a second end region, and a middle region there between, a keyboard mounted to only the first end region, and a portable ultrasound scanner support mounted to only the second end region, wherein the portable ultrasound support comprises at least one mechanical connector, and the base portion of the first dock is configured to support the first common portion of the first dock relative to a first surface, and wherein the first common portion of the first dock further includes one or more electrical connectors;

a second dock including a first common portion and a base portion, wherein the first common portion of the second dock includes a support arm with a first end region, a second end region, and a middle region there between, a keyboard mounted to only the first end region, and a portable ultrasound scanner support mounted to only the second end region, wherein the portable ultrasound scanner support comprises at least one mechanical connector, the base portion of the second dock is configured to support the first common portion of the second dock relative to a second surface and wherein the first common portion of the first dock and the first common portion of the second dock are the same and the base portion of the first dock and the base portion of the second dock are different, and wherein the first common portion of the second dock further includes one or more electrical connectors; and a first portable ultrasound scanner including an ultrasound transducer interface, a display on a first side of the scanner, at least one complementary mechanical connector and electrical connectors on a second side of the first scanner which is opposite the first side and which is configured to attach the first portable ultrasound scanner to the at least one mechanical connector and electrical connectors, and a dock interface that selectively connects the first scanner to the first and second docks for operation in conjunction therewith.

2. The apparatus of claim 1 including a second portable ultrasound scanner including an ultrasound transducer interface, a display on a first side of the scanner, at the first side, and which is configured to attach the second portable ultrasound scanner to the at least one mechanical connector, and a dock interface that selectively connects the second scanner to the first and second docks for operation in conjunction therewith, wherein the first scanner performs a first set of functions and the second scanner performs a second set of functions, and the first set is a subset of the second.

3. The apparatus of claim 2 wherein the first set includes a digital information and communication in medicine function and a communication and color flow mode function and the second set includes a three dimensional image display function and a brachytherapy function.

4. The apparatus of claim 1 wherein the first portable ultrasound scanner includes a single element mechanical transducer interface and the first scanner is configured to present information indicative of information received from the single element mechanical transducer on the display.

5. The apparatus of claim 4 wherein the first portion of the first dock includes an output that presents a video signal indicative of an image indicative of the received information from the first scanner.

6. The apparatus of claim 1 wherein the first portable ultrasound scanner includes a physiological variable transducer interface and the first scanner is configured to present information indicative of information received from the physiological variable transducer interface on the display.

7. The apparatus of claim 6 wherein the information includes information indicative of at least one of blood pressure, respiration, or a cardiac characteristic.

8. The apparatus of claim 1 wherein the keyboard of the first dock and the keyboard of the second dock are identical.

9. The apparatus of claim 8 wherein the first portion of the first dock and the first portion of the second dock are mechanically identical and the one or more electrical connectors of the first portion of the first dock and the one or more electrical connectors of the first portion of the second dock are identical.

10. The apparatus of claim 1 wherein the first dock includes a wheeled floor dock and the second dock includes a wall dock or a ceiling dock.

11. The apparatus of claim 1 wherein the first dock is a floor dock including a vertical post that supports the common portion above the floor and the first dock includes a printer mounted behind the post.

\* \* \* \* \*